(12) United States Patent
Valletta

(10) Patent No.: US 7,291,625 B2
(45) Date of Patent: Nov. 6, 2007

(54) USE OF A VITAMIN COMBINATION FOR THE TREATMENT OF PRURITUS AND NON-INFECTIVE DISORDERS INVOLVING ITCHING AND/OR INFLAMMATION

(76) Inventor: Giampero Valletta, Via Campidoglio, 188, I-03024 Ceprano (IT)

( * ) Notice: Subject to any disclaimer, the term of this patent is extended or adjusted under 35 U.S.C. 154(b) by 111 days.

(21) Appl. No.: 11/342,903

(22) Filed: Jan. 30, 2006

(65) Prior Publication Data

US 2006/0178368 A1 Aug. 10, 2006

Related U.S. Application Data

(62) Division of application No. 10/009,225, filed as application No. PCT/IT00/00196 on May 17, 2000, now Pat. No. 7,026,319.

(30) Foreign Application Priority Data

May 17, 1999 (IT) .............................. RM99A0309

(51) Int. Cl.
- A01N 43/40 (2006.01)
- A01N 43/54 (2006.01)
- A61K 31/435 (2006.01)
- A61K 31/505 (2006.01)

(52) U.S. Cl. ..................... 514/277; 514/267
(58) Field of Classification Search ................. 514/277, 514/267
See application file for complete search history.

(56) References Cited

U.S. PATENT DOCUMENTS 4,619,829 A 10/1986 Motschan 5,496,827 A * 3/1996 Patrick ........................ 514/310
6,248,763 B1 * 6/2001 Scivoletto ................... 514/356

FOREIGN PATENT DOCUMENTS

FR 2 096 712 A 2/1972
WO WO 94/27624 A 12/1994

OTHER PUBLICATIONS

International Search report, Nov. 14, 2000.
Otrokov A.N., "New methods of vitamin B treatment of itching dermatoses in middle aged patientsi Novye metody B-vitaminoteraoll bol'nykh zudiaschimi dermalozami v pozhliom l starcheskom vozraste." Vestnik Dermatologii l Venerologii, Dec. 12, 1997, pp. 62-65, XP000961650.
Fuchs J., "Vitamins and Skinl. Vitamine Und Haut.", Therapeutische Umschau. 1994, vol. 51, No. 7, pp. 489-495, XP000961735.

* cited by examiner

Primary Examiner—Cecilia J. Tsang
Assistant Examiner—GiGi Huang
(74) Attorney, Agent, or Firm—Hedman & Costigan PC; James V. Costigan

(57) ABSTRACT

Use of a combination of two vitamin compounds, i.e. riboflavin (also known as vitamin $B_2$) and nicotinic acid (also referred to as niacin) or, as an alternative thereto, the corresponding amide, i.e. nicotinamide or niacinamide (also known as vitamin PP) for the systemic treatment of various forms of itching, such as, e.g., pruritus associated with renal insufficiency or failure (i.e. uremic pruritus), and of pruritus forms that are not connected with primary organic affections, as well as for the treatment of a number of non-infective internal affections of a substantially inflammatory nature, such as e.g., urticaria and/or angioedema, asthma, allergic rhinitis and allergic oculorhinitis.

3 Claims, No Drawings

USE OF A VITAMIN COMBINATION FOR THE TREATMENT OF PRURITUS AND NON-INFECTIVE DISORDERS INVOLVING ITCHING AND/OR INFLAMMATION

This application is a divisional application of Ser. No. 10/009,225, filed May 17, 2000 which claims priority to Italian application Ser. No. RM99A000309, filed May 17, 1999 and PCT application PCT/IT00/00196, filed May 17, 2000.

SPECIFICATION

The present invention concerns the use of a vitamin combination for the treatment of pruritus and non-infective disorders involving itching and/or inflammation. More particularly, this invention relates to the use of a combination of two vitamin compounds, i.e. riboflavin (also known as vitamin $B_2$) and nicotinic acid (also referred to as niacin) or, as an alternative thereto, the corresponding amide, i.e. nicotinamide or niacinamide (also known as vitamin PP) for the systemic treatment of various forms of itching, such as, e.g., pruritus associated with renal insufficiency or failure, or forms of itching the etiology of which is not connected with organic lesions or with other primary pathologies, as well as for the treatment of a number of non-infective internal affections of a substantially inflammatory nature.

As it is known, the cutaneous sensation currently referred to as itching may be considered as a uniform response to a wide variety of physical and chemical stimuli, which may be of an endogenous or exogenous nature. Such stimuli act on the receptors of the free nerve endings located at the dermalepidermal junction and around the hair follicles. It is currently believed that pain, temperature and touch are all sensations transmitted through the same pathways of non-myelinated free nerve fibers innervating human skin. A low-intensity stimulation of such fibers would cause pruritus while a more intense stimulation would turn into a real pain sensation. While being transmitted through the same sensory fibers, the neural impulses of itch have a frequency quite lower than the pain impulses; however, if scratching follows as a response to the itch stimulus, the frequency of the neural impulses increases with the intensity of scratching, and the corresponding sensation turns from itchy into painful.

As pointed out in the foregoing, itching may be induced by a great variety of circumstances, both physiologic and pathologic. Especially when it is generalized and associated with cutaneous lesions, such as vesicles and papules, itching is often the effect of a primary dermatological disease, and in many cases it represents the fundamental symptom for diagnosis. In the absence of cutaneous lesions, on the other hand, itching may originate in many cases from systemic disorders such as, e.g., neoplastic diseases, metabolic or endocrine disorders, renal, hematological or hepatic diseases, or also from allergic reactions, or from hypersensitivity to some medicaments. Lastly, in other cases itching appears to be the sole dominant chronic symptom, with no possibility of any clarification on the etiopathogenesis of this affection. In such cases, itching is normally referred to as "sine materia" pruritus, i.e. it represents a symptom of an unknown origin, which is not classifiable in the absence of identifiable cutaneous or extracutaneous alterations. The only objective, albeit secondary, signs of the concerned disorder are limited to traces of scratching such as linear excoriations and, if the situation lasts for a longer time, small secondary papules (i.e. papules due to scratching) and lichenification signs with hyperpigmentation in the most chronic cases.

The group of "sine materia" pruritus includes the itching manifestations occurring, without any connection with organic lesions or with systemic or skin diseases, in the external genital areas (such as vulvar and scrotal pruritus) and in the perianal area (scientifically referred to as pruritus ani), as well as pruritus of aged skin (i.e. senile pruritus). The latter is a generalized affection quite diffused among persons aged 65 or over. In this case, once the possible occurrence of skin diseases such as scabies, bullous pemphigoid, lichen planus and eczema, or the occurrence of systemic diseases characterized by pruritic symptomatology, such as those mentioned in the foregoing, have been excluded, the itching sensation has to be ascribed, actually, to the so-called pruritus of aged skin. Such condition is considered to be a consequence of desiccation of the skin. A dehydrated skin, generally combined with exposure to ambient conditions of low humidity and temperature, induces fine cracking and scaling in the skin of the elderly subject, with consequent diffused and persistent itching.

The actual pathway through which the itching reaction is elicited has been investigated in several detailed studies, and several chemical mediators of itch, such as histamine, kallikrein, PAFs (platelet activating factors) and various endopeptidases (e.g., papain, trypsin, erythrocyte proteases, mast cell proteases, lysosomial enzymes) have been identified to date. In spite of that, the mechanism of itch induction has not been fully clarified at present. It is essentially for this reason that some agents successfully employed against some forms of itching, such as, e.g., antihistamines or steroidal drugs, are totally ineffective against other forms. The therapeutic approach adopted so far for the treatment of the "sine materia" pruritus forms, in particular for the treatment of senile pruritus and of itching of the anal and genital areas, consists of topically applying corticosteroidal drugs, antihistamines and skin moisturizers. However, none of these remedies turned out to be appreciably effective in the concerned cases.

Another type of pruritus against which, at present, no valid therapy has been found, in spite of the abundant information available about the supposed causes thereof, is the pruritus connected with renal insufficiency, usually referred to as uremic pruritus. The latter is one of the most distressing symptoms of renal insufficiency, affecting about 80% of the patients on renal dialysis, and is currently believed to be due to the building up of some pruritogenic substance in the body. Patients with chronic renal failure often exhibit cutaneous dryness, anemia, defects of homeostasis such as haematomas and ecchymoses, and secondary hyperparatyroidism (with itching and lesions due to scratching). The abundant use of emollients rarely results in significant relief. In some cases the symptoms are reduced when the patient undergoes dialysis, thereby suggesting that a pruritogenic substance has been removed. However, in many cases itching persists even after dialysis, and resists to all therapeutic attempts, both systemic and topical. Also against such types of pruritus the current therapeutic approaches consist of the administration of antihistamines or corticosteroids, mostly without any appreciable success.

It is therefore one object of the present invention to provide a therapeutic remedy effective for the treatment of the "sine materia" pruritus forms, as well as for the treatment of uremic pruritus, which allows to successfully resolve, by means of a pharmacological therapy consistently effective and free from adverse effects, such hitherto unresolved pathologic conditions. To achieve such purpose, in the frame of the research that lead to present invention, a particular combination of vitamins has been considered, i.e. the combination of nicotinic acid, i.e. 3-pyridinecarboxylic acid, also known as niacin (or, in the alternative thereto, the corresponding amide, i.e. nicotinamide, also known as vitamin PP) and riboflavin (also known as vitamin $B_2$).

The first ingredient of the above combination, i.e. nicotinic acid, is a well-known vitamin, naturally occurring in several animal and vegetal tissues, particularly in food sources such as meat, poultry, fish, liver, kidney, eggs, nuts, butter, milk and yeast. In human beings, nicotinic acid may also be synthesized from the amino acid tryptophan, but the latter source is normally insufficient to satisfy the dietary requirements for this vitamin. Actually, the alternative name vitamin PP (or P.P. factor, i.e. pellagra preventive factor) by which the said agent is known is due to its critical activity in the prevention of pellagra. The latter is a disease caused by vitamin deficiency, that occurs in dietary regimens poor in tryptophan (or, correspondingly, in niacin or in nicotinamide), such as a diet substantially based on maize and with a poor intake of animal proteins.

Nicotinic acid functions in the body only after conversion to either one of the physiologically active forms nicotinamide adenine dinucleotide (NAD) or nicotinamide adenine dinucleotide phosphate (NADP). These serve as coenzymes for a wide variety of proteins that catalyze oxidation-reduction reactions essential for tissue respiration. Such biological process is actually the result of several oxidation-reduction reactions occurring within the cells, in particular in the mitochondria, aimed at oxidizing that part of material reaching the cells (through the blood circulation) in order to be employed for energy production. Among the various enzymes responsible for the oxidative processes (i.e. oxidoreductases), that perform their function by accepting a $H_2$ molecule from the substrate, the enzymes referred to as dehydrogenases cannot employ molecular oxygen as an immediate acceptor of the hydrogen taken from the substrate, but have to use the pyridine coenzymes (i.e., NAD and NADP) as acceptors. Therefore, the presence of the said coenzymes is of a critical importance for the proper development of the biochemical cycles that produce energy from, e.g., sugars (i.e., glycolysis and Krebs cycle) or from fatty acids (i.e., beta-oxidation), and in the metabolic pathway leading to urea (ornithine cycle).

In view of the foregoing, the presence of suitable levels of nicotinic acid and/or niacinamide (or tryptophan) in the body is an essential requirement for a healthy skin, for the regular function of the gastrointestinal tract, for the maintenance of the nervous system as well as for the synthesis of the sex hormones. Symptoms of deficiency may be muscular weakness, generalized asthenia, loss of appetite, cutaneous eruptions, stomatites, insomnia, nausea and migraine. As pointed out in the foregoing, a severe deficiency leads to pellagra. The dosages of nicotinic acid, nicotinamide or suitable derivatives (such as methyl nicotinate) normally employed for the treatment of pellagra are of about 50 mg, by the oral route, up to ten times daily. In the event that the oral administration is impossible, intravenous injection of 25 mg of vitamin may be given two or more times daily.

It is also known that nicotinic acid and nicotinamide are effective in improving blood circulation and in lowering cholesterol levels. As far as the first mentioned effect is concerned, some products for topical administration containing nicotinic acid are available, having the function of topical rubefacient and analgesic, for the relief of muscular pain and rheumatism. In these products niacin assumedly performs the function of enhancing peripheral blood circulation, as it dilates the subcutaneous blood vessels after penetrating the skin.

As far as the second effect mentioned above is concerned, niacin is employed for systemic administration, i.e. by the oral or the parenteral route, at dosages quite above the dosage required for the prophylaxis and therapy of pellagra (namely, from 2 to 6 g per day) in preparations intended for the therapy of hyperlipidemia, for lowering cholesterol levels in the blood. At the large doses required for this therapeutic indication, however, both nicotinic acid and nicotinamide have shown a number of adverse side effects, including gastrointestinal disturbances (such as abdominal pain and nausea) hepatotoxicity, and, above all, flushing (cutaneous erythema) often accompanied by warmth, tingling and itching.

In order to reduce the said side effects while keeping the high dosages required for the antilipemic therapy, there have been proposed modifications of the nicotinic acid molecule, resulting in various derivatives thereof, as well as combinations of niacin or nicotinamide with other active ingredients or adjuvants, specific dosage forms and formulations. An example of such modifications is disclosed in EP-A-0349235 (and in the corresponding U.S. Pat. No. 4,965,252), concerning an oral antihyperlipidemic composition of nicotinic acid wherein the active ingredient is mixed with guar gum and, optionally, with food-grade organic acids and/or pharmaceutically acceptable mineral salts, as well as other suitable adjuvants. The combination with guar gum reportedly affords a preparation for oral administration which eliminates the undesirable flushing and itching side effects of high dose niacin while effectively lowering cholesterol levels. In addition, the proposed combination is said to only require an effective dosage of niacin of 1.2-1.5 g per day, lower than the recommended daily dose of niacin when used alone as an antilipemic agent.

Another example of systemic preparation exploiting the activity of nicotinic acid for the treatment of hyperlipidemias while attempting, at the same time, to reduce the adverse side effects thereof, is disclosed in the international patent application WO-A-9632942. The latter discloses a combination of a hypolipemic amount of nicotinate with a non-steroidal anti-inflammatory drug (NSAID), preferably in a sustained release form. According to the disclosure, the NSAID is effective in reducing the flushing side effect associated with the use of niacin when administered as an antilipemic agent.

In spite of the fact that one of the most usual adverse effects of high dosage nicotinic acid and niacinamide is itching, the concerned agents have also been proposed, mostly in preparations for topical administration, for use in the therapy of cutaneous affections wherein itching is one of the typical symptoms. For instance, the international patent application WO-A-9852297 discloses dermatological and cosmetic compositions based on nicotinamide, niacin, or ester derivatives thereof (methyl nicotinate being particularly preferred), which are applied topically on the skin to treat a number of skin conditions including acne, age spots, fungi, itching, pain and itching from insect bites, cellulite, varicose veins, stretch marks and burns. The list of affections that may be treated with the claimed composition, in addition to being extremely generic, is not supported by any experimental data, nor any chemical test is reported that may allow to evaluate the therapeutic effects obtained with the use of the topical preparation disclosed.

On the other hand, the use of nicotinamide or nicotinic acid for the treatment of acne vulgaris, both by topical and by systemic administration, has previously been disclosed in the U.S. Pat. No. 4,505,896. As far as the oral therapy is concerned, said document proposes the oral administration of dosages comprised between 100 and 600 mg per day (in divided doses taken two to four times daily). Such doses of niacin/nicotinamide are, actually, of the same order of magnitude as the dose required for therapy or prophylaxis of vitamin PP deficiency, and the problem of the flushing side effect is apparently not relevant at such low doses.

In the frame of the studies that lead to the instant invention, it has been ascertained, as a first step, that the systemic administration of niacin or niacinamide at dosages quite lower than for the therapy of hypercholesterolemia— namely at the dosage typically employed in the use of the same agents for the prevention and therapy of pellagra—on one hand does not lead to the undesired side effects of flushing and itching reported for the high dosages but, on the other hand, is not appreciably effective in combating the pruritus forms referred to in the foregoing. As a matter of fact, according to the clinical experimentation carried out and partially reported further on, uremic pruritus and itch affecting patients on renal dialysis, as well the "sine materia" pruritus forms (such as pruritus ani, pruritus vulvae, and pruritus senilis) did not show to be sufficiently responsive to the administration of preparations based on nicotinamide or niacin alone.

It has been found, however, that the desired effect is obtained when niacin or nicotinamide are administered systemically in combination with another known vitamin compound, i.e. riboflavin or vitamin $B_2$.

In this connection, the U.S. Pat. No. 5,496,827 teaches compositions for topical application on the skin, wherein the main active ingredient, i.e. methyl nicotinate, may be combined with various vitamins, minerals and other nutrients, including, inter alia, riboflavin. The resulting topical compositions are proposed for use in the treatment of various conditions that may be treated by means of topical applications to the affected areas, such as muscular pain, acne, eczema, or for stimulating the hair growth, removing senile lentigines (brown spots) and enhancing fingernail growth. Also in this case, the prior art points out that an excessive increase of the methyl nicotinate level "tends to produce a rather pronounced pruritus (itching of the skin)". The concerned document, however, mentions riboflavin as one of the many vitamins and trace elements that may be added to methyl nicotinate in order to be carried through the skin by transdermal delivery, as the alleged function of methyl nicotinate is to promote transdermal delivery.

With reference to the second active ingredient of the present invention, i.e. riboflavin (7,8-dimethyl-10-(D-ribo-2,3,4,5-tetrahydroxypenthyl)isoalloxazine, also such compound is a nutritional factor of a primary importance, that is found mainly in milk, eggs, cheese, liver, heart, kidney and leafy vegetables. Riboflavin carries out its biological function in the body in the form of one or the other of two coenzymes, i.e. riboflavin phosphate, commonly called flavin mononucleotide (FMN), and flavin adenine dinucleotide (FAD). Similarly to the two pyridine coenzymes referred to in the foregoing (i.e., NAD and NADP), FMN and FAD co-operate with the respiratory flavoproteins in oxidizing the substrate by accepting a hydrogen molecule from the substrate. Contrary to NAD and NADP, however, FMN and FAD may yield said hydrogen directly to molecular oxygen. In addition, the oxidoreductive potential of FMN and FAD is such that these two compounds can oxidize the reduced pyridine coenzymes: actually, the function of flavoproteins (having, as pointed out before, FAD and FMN as coenzymes) is on one hand to directly oxidize the substrates and, on the other hand, to assist in the function of the pyridine enzymes, by reoxidizing them once they have become reduced by reaction with a substrate.

In view of the foregoing, considering that, in practice, the pyridine coenzymes (NAD and NADP) can perform their function only in the presence of flavoproteins, and thus in the presence of riboflavin, it will be apparent that the presence of both niacin and riboflavin is necessary for an efficient working of the biochemical mechanisms governing the cellular metabolism. Without wishing to be bound by any particular theory concerning the mechanism of action of the proposed combination of active agents, it is postulated that both niacin and riboflavin play a critical role in the metabolism of the mast cells. A deficiency of any one of the said agents would negatively affect the energy-production step of the metabolic chain leading to activation of these cells, that is mostly responsible for the release of biochemical mediators of the itching and inflammatory responses. As known, mast cells are found in organs rich in connective tissue, such as the skin and the respiratory and gastrointestinal tracts, and are characterized by the presence of granules that may be secreted by the mast cell upon activation of the latter, thus releasing a number of the above mentioned mediators, including histamine.

According to the present invention, it has been considered that once the mast cells are activated—by a variety of mechanisms, including binding of their membranes with immunoglobulins E (IgEs) and exposure of the mast cell to an antigen—there occurs within the mast cell a series of enzymatic reactions comprising an energy-requiring step and ending with the degranulation of the mast cells and the release of preformed or newly-generated mediators. The preformed mediators, that are stored in the above-mentioned granules, include histamine (which, inter alia, causes smooth muscle contraction and itching, enhances the venular permeability and increases the airway resistance), while other unstored mediators, that are generated upon activation of the mast cells and have the capacity to alter the venular permeability and to contract smooth muscles in a variety of organs, include SRS-A (slow-reacting substance of anaphylaxis) and PAFs (platelet activating factor(s)).

In view of the foregoing, in the light of the clinical tests results presented further on, it may reasonably be postulated that both the "sine materia" pruritus forms, which are not due to any primary dermatological or internal affection, and uremic pruritus, which is a manifestation of unknown etiology connected with renal insufficiency, are caused by some energy-controlled alterations in the metabolic pathway leading to the secretion of biochemical mediators from mast cells, and that the systemic administration of a suitable dosage of niacin or nicotinamide and riboflavin would provide the body with the necessary amounts of NAD/NADP and FAD/FMN to properly modulate the mast cells activity.

As a further object of the instant invention, other affections of a non-infective etiology characterized by itching and/or inflammation (phlogosis) such as, e.g., urticaria and angioedema, bronchial asthma, allergic rhinitis and ocu-lorhinitis, have been considered, in the light of the above etiopathogenetic theory, in order to provide a systemic therapy exploiting the same combination of active ingredients.

As it is known, urticaria is a pruritic dermatosis characterized by the formation of circumscribed, raised, erythematous and usually pruritic areas of edema. Such lesions have a rosy-red appearance with a white central area, and are surrounded by an erythematous halo. The single wheals may have a round, elliptic or variously contoured shape, and may evolve in a few days or weeks (acute urticaria) or in several weeks or months (chronic urticaria). When the edematous process extends into the dermis and/or subcutaneous or submucosal layers, the relevant affection is known as angioedema. Urticaria and angioedema may occur in any position together or individually. Both affections may be due to several etiologic factors of an immunologic nature (such as, e.g., hypersensitivity to pollens, foods, drugs, etc.), or of a non-immunologic nature (e.g. non-IgE-dependant intolerance to various therapeutic and diagnostic agents, such as the well-known reactions to aspirin and related non-steroidal anti-inflammatory agents). However, in the great majority of cases, urticaria/angioedema is of unknown cause, and is currently referred to as idiopathic urticaria.

Asthma is a respiratory disorder characterized by recurring episodes of dyspnea, wheezing, coughing and viscous mucoid bronchial secretions, caused by obstruction of the airways by excessive mucous production and edema of the respiratory mucosa. These reactions are believed to result from an increased sensitivity of the bronchial tree to stimuli of various origin, such as physical or emotional stress, inhalation of powders or pollutants or contact with allergens or with some drugs. Also in this case, the pathogenesis of the disease is unclear, and the actual mechanism by which asthma develops is unknown. However, according to the most diffused position, bronchial asthma is to be considered an inflammatory disease. In particular, allergic asthma is caused by the exposure of the bronchial mucosa to an inhaled airborne antigen. The latter causes the production of antibodies (IgEs) that bind to mast cells thereby activating such cells as explained in the foregoing. The release of histamine by the activated mast cells stimulates contraction of the bronchial smooth muscle and causes mucosal edema. The current therapy for asthma may include elimination of the causative agent, aerosol or oral bronchodilators, beta-adrenergic drugs, methylxanthines, sodium cromoglycate and short term use of corticosteroids.

Allergic rhinitis is an inflammation of the nasal passages, usually associated with nasal obstruction and discharge, as well as itching of the nose, caused by a localized sensitivity reaction to an allergen like dust, animal dander, or an antigen such as pollen. When the itching symptom extends to the eyes, accompanied by lachrymation, the disease is more properly referred to as oculorhinitis. The conventional treatments include the topical or systemic administration of antihistamines, avoidance of the antigen and hyposensitization by injection of diluted antigen in gradually increasing amounts.

In accordance with the invention it has been found that the above affections, as well as other affections characterized by a substantially inflammatory nature and often accompanied by the itching symptom, may be successfully treated by means of the systemic administration of the proposed vitamin combination.

Accordingly, the present invention specifically provides the use of a combination of nicotinic acid or nicotinamide with riboflavin for the manufacture of a medicament not comprising as the active ingredients any other anti-inflammatory agent or any other vitamin agent besides said nicotinic acid or nicotinamide and said riboflavin, said medicament being suitable for systemic administration, for the treatment and/or the prophylaxis of pruritus and non-infective, non-neoplastic, non-rheumatic disorders involving itching and/or inflammation. Specifically, the forms of pruritus against which the proposed combination is particularly effective include itch associated with renal insufficiency or failure (i.e. uremic pruritus) and pruritus forms that are not connected with primary organic affections, such as itching of aged skin (i.e., senile pruritus), vulvar pruritus, scrotal pruritus and anal pruritus. As to the non-infective disorders involving itching and/or inflammation, the proposed combination is particularly useful for combating urticaria and/or angioedema, asthma, allergic rhinitis and allergic oculorhinitis.

For the therapeutic indications according to the present invention, the two active ingredients are to be systemically administered at a dosage comprised between 0.5 and 750 mg/day of niacin or of nicotinamide and between 0.1 and 250 mg/day of riboflavin. Preferably, the said combination consists of nicotinic acid or nicotinamide and riboflavin in a ratio by weight of from 40:1 to 10:1 (nicotinic acid or niacinamide:riboflavin), optionally in a pharmaceutically acceptable vehicle or carrier suitable for systemic administration. The preferred ratio is 20:1 (niacinamide:riboflavin). According to a particularly effective therapeutic protocol, 50 mg of nicotinamide+2.5. mg of riboflavin are orally administered twice daily, and the treatment is continued until the itching or the inflammatory affection has totally disappeared. Thereafter, in some particular instances, the treatment is continued with half the dosage of the vitamin combination, for about 15 more days.

The compounds according to the invention may be administered through different systemic routes, e.g. orally or parenterally. For such types of administration the active ingredients may be incorporated in conventional pharmaceutical preparations, in solid or liquid dosage forms. The latter may contain the adjuvants usual in the pharmaceutical art such as, for instance, sweeteners, flavors, colors, coatings and preservatives, inert diluents such as calcium carbonate, sodium carbonate, lactose and talc, binders such as starch, gelatin and polyvinylpyrrolidone, suspending agents such as methyl cellulose or hydroxyethyl cellulose and wetting agents such as lecithin, poly-oxyethylene stearate and poly-oxyethylene sorbitan monooleate, reducing agents such as ascorbic acid and salts thereof. The preparations for parenteral administration (in particular, to be injected through the intravenous or the intramuscular route) may also contain the active ingredients dissolved or suspended in distilled water, together with the common pharmaceutically acceptable excipients.

A particularly effective therapeutic protocol according to the invention, for the treatment of all of the itching and inflammatory forms specified above but uremic pruritus is as follows: $1^{st}$ phase: 50 mg of nicotinamide+2.5 mg of riboflavin twice daily by oral administration, up to the total disappearance of the symptom; then continue with 50 mg of nicotinamide+2.5 mg of riboflavin once daily for 15 days; $2^{nd}$ phase (optional): 50 mg of nicotinamide+2.5 mg of riboflavin once daily for 15 days a month, for prophylactic purposes. It is advisable to take the medicament by the oral route, after the main meals, with abundant water (at least half a glass). In the event that the treatment is discontinued and the symptoms revert, it is necessary to start again from the $1^{st}$ phase.

A therapeutic protocol suited to the treatment of uremic pruritus (without dialysis) is as follows: $1^{st}$ phase: 50 mg of nicotinamide+2.5 mg of riboflavin twice daily by oral administration, up to the total disappearance of pruritus; then continue with 50 mg of nicotinamide+2.5 mg of riboflavin three times a week; $2^{nd}$ phase (optional): 50 mg of nicotinamide+2.5 mg of riboflavin three times a week for 15 days a month. Also in this case, the preferred form of administration is the oral form, and also in this case if the therapy is discontinued and itching appears again, the protocol will have to be restarted from the beginning. In the treatment of uremic subjects who currently undergo dialysis the protocol is the same as for the $1^{st}$ phase above, but the continuation of the treatment with half the dose will take place starting after each dialysis treatment (also in this case, after the meal and with abundant water).

As pointed out before, as an alternative to oral administration the parenteral route may be exploited, with a preferred dosage of 20 mg of nicotinamide and 1 mg of riboflavin once or twice daily.

According to another specific aspect thereof, the present invention provides a composition for systemic administration for the treatment and/or the prophylaxis of pruritus and non-infective, non-neoplastic, non-rheumatic disorders involving itching and/or inflammation, containing, as the active ingredients, a combination of nicotinic acid or nicotinamide with riboflavin and free from any other vitamin agent and any other antiinflammatory agent besides said nicotinic acid or nicotinamide and said riboflavin. Particularly preferred features of the said compositions are recited in the dependent claims. It is evident, however, that the two active ingredients of the invention do not necessarily have to be contained in a single preparation, as they can be administered separately, provided that the dosage and therapeutic protocol are as prescribed in the foregoing.

Some experimental results obtained according to the present invention, including clinical data concerning the performance of the proposed combination in comparison with the use of nicotinic acid or nicotinamide alone, are reported below for merely illustrative purposes.

$1^{st}$ Series of Tests—Treatment with the Nicotinamide-riboflavin Combination $1^{st}$ case—67-year-old male subject in renal dialysis three times weekly—At the start of the test, the patient had been on dialysis three times a week for about two years, each treatment lasting 4 hours. For about 4 years, the patient had been complaining of a diffused itching. The latter was quite moderate at the beginning, but had been gradually increasing in intensity, and had become quite unbearable. Upon interviewing the specialists responsible for the renal treatment, he was given antihistamines for about six months with no appreciable result. As a consequence, the patient had discontinued the anti-histamine treatment.

Thereafter, the patient was treated with 50 mg of nicotinamide+2.5 mg of riboflavin twice daily, by oral administration. After 5 days from the start of this therapy, itching had disappeared. The patient continued the same therapy for about 15 days, and thereafter the dosage was reduced to one-half, the administration occurring after the dialysis treatment. The subsequent checks, performed every month, showed that itching had totally disappeared.

$2^{nd}$ case—65-year-old male subject with chronic renal failure—The patient had been suffering from chronic renal failure for about 4 years. The nitrogen level of his blood was 105 mg/dl, while the level of his serum creatinine was 3 mg/dl. The patient was being treated by a nephrologist. About 15 months before, he started to report a diffused increasing pruritus, that had become unbearable about 9 months before. Every therapeutic approach proposed and carried out by the kidney specialist resulted in no appreciable relief.

The patient was then treated orally with a combination of 50 mg of nicotinamide+2.5 mg of riboflavin twice daily. After 6 days itching had totally disappeared, and the treatment was continued for 10 days more. Thereafter, the dosage was reduced to one half, still administered by the oral route, for 15 days a month. At the subsequent checks, carried out every month, the patient reported a total absence of itching.

$3^{rd}$ case—67-years-old female subject with senile pruritus—The patient had been complaining for about 3 years of a diffused itching, which had become increasingly intense. At first, she consulted her physician, who addressed her to a dermatologist. As no cutaneous pathologies had been evidenced, the patient was visited by a specialist in internal medicine, who diagnosed a senile pruritus and prescribed some hygienic measures and antihistamines, from which the patient had drawn no benefits.

The patient was then treated by oral administration of 50 mg of nicotinamide+2.5 mg of riboflavin twice daily. After 5 days the itching had totally disappeared, and the treatment was continued for 10 days more. Thereafter, the therapy was reduced to half the dosage, for 15 days a month. At each subsequent check-up, the patient did not report any itching.

$4^{th}$ case—46-years-old female subject with anal and vulvar pruritus—The localized symptomatology was quite severe since about two years before. As a first attempt, a gastroenterologist had been consulted for the anal itching, and thereafter a gynaecologist had been consulted for the vulvar itching. Neither specialist could detect any objective disorder falling within his competence. In order to mitigate the disturbance, various topical treatments with non-steroidal anti-inflammatory drugs, corticosteroids and antimycotic agents had been prescribed, as well as a systemic treatment with antihistamines. No treatment brought about any improvement in the patient's condition.

The patient was then treated with 50 mg of nicotinamide+2.5 mg of riboflavin twice daily, by oral administration, and after 7 days itching had disappeared. The treatment was continued for 12 more days, and then it was reduced to half the dosage, for 15 days a month. At each subsequent monthly check-up the patient always reported a total absence of itching.

$5^{th}$ case—50-years-old male subject with acute urticaria.—After collecting mushrooms in a wood, the patient had been complaining for eight days of a serious itching at his forearms and torso. At the clinical examination, the patient showed, both on his forearms and on the front and back of his chest, erythematous circumscribed lesions having wavy margins, remarkably raised with respect to the rest of the surrounding skin. Traces of superficial lesions were present, apparently due to scratching. Upon being diagnosed an acute urticaria, the patient was treated with systemic antihistamines and corticosteroids, from which he could not draw any benefit.

The patient was then treated orally with 50 mg of nicotinamide+2.5 mg of riboflavin twice daily. After 2 days the patient's condition had already remarkably improved, and after 3 more days itching had entirely disappeared, although some moderate erythematous lesions were still visible. In this case the therapy was continued for 10 more days and then it was finally discontinued.

$6^{th}$ case—46-years-old female subject with recurrent urticaria—The patient, who lives in the countryside, had been complaining for 15 years of a phytodermatitis that manifested itself with episodes of urticaria. The latter appeared with itching and reddish wheals of 3-4 cm diameter, diffused, initially, only on the parts of the body that came in contact with an unidentified grass, and progressively extending to the rest of the body. When such episodes, usually lasting for 12 days, occurred, the patient used to take antihistamines and corticosteroids, however with no appreciable relief.

Then, at the beginning of one of such episodes of urticaria the patient was administered, by oral route, 50 mg of nicotinamide+2.5 mg of riboflavin twice daily. As a result, itching decreased and disappeared in the following 4-5 days. Thereafter, the patient continued to take half a dose of the above agents for 15 days a month, and the subsequent contacts with the grass of her garden did not result in any skin discomfort.

7th case—28-years-old female subject with bronchial asthma—The patient had been suffering for about 10 years from recurrent episodes of bronchial asthma, in the spring period (i.e., from April to June). During each of said episodes, the patient experienced coughing, expiratory dyspnea, suffocation feeling. At the end of said episodes, that usually lasted about one hour, the patient excreted a dense and viscous material. She used to take antihistamines regularly in spring, sometimes in combination with theophyllins, with a quite poor relief.

Starting from mid-March, the patient was then treated with 50 mg of nicotinamide+2.5 mg of riboflavin, twice daily, by oral administration. The treatment was continued as such for 4 months on end and then discontinued. No episodes of bronchial asthma occurred during the whole spring period.

8th case—32-years-old male subject with bronchial asthma—The patient had started to suffer from respiratory disturbances (i.e. coughing, dyspnea) since he was 15. Such disturbances entailed a diagnosis of bronchial asthma. They appeared in the late spring (i.e. mid-April) and lasted until the end of June. Since the said diagnosis was made, the patient was treated with antihistamines. Corticosteroids and theophyllins were administered during the acute episodes. Such therapy had constantly resulted in a partial result.

The patient was then orally treated, starting from mid-April, with 50 mg of nicotinamide+2.5 mg of riboflavin twice daily, for 3 months on end. During the said spring period, no episodes of asthma were ascertained. Thereafter, the therapy was discontinued until the following spring.

9th case—40-years-old male subject with allergic oculorhinitis—The patient suffered from allergic oculorhinitis, which manifested itself with sneezing, lachrymation, pharyngeal pain. He was also allergic to gramineae. The symptoms started in April and lasted until June. He had been treated with antihistamines during the critical period, but the symptoms, in spite of the treatment, were only attenuated.

The patient was then treated, starting from the beginning of April, with 50 mg of nicotinamide+2.5 mg of riboflavin twice daily, by oral administration. The treatment was continued for 15 days, and then the dosage was reduced to one half up to the end of June. During this period no symptoms of allergy were detected.

10th case—12-years-old male subject with allergic rhinitis—The patient had been suffering for 6 years from allergic rhinitis, the symptoms of which were nasal discharge, sneezing and nasal obstruction. Such symptoms occurred in spring and during this period the patient was treated, with unsatisfactory results, by antihistamine therapy.

Starting from mid-March, the patient was then treated with oral administration of 50 mg of nicotinamide+2.5 mg of riboflavin twice daily. The same dosage was administered for 10 days, and then it was reduced to one half, and continued up to the end of June. During the whole period, the patient reported no symptoms that could be ascribed to allergic rhinitis.

2nd Series of Tests—Treatment in Two Phases: First with Nicotinamide Only and with the Nicotinamide-riboflavin Combination 1st case—78-years-old male subject on renal dialysis three times weekly—The patient had been on dialysis three times a week for about 3 years, each treatment lasting 4 hours. For about two years and a half the patient had been complaining of a diffused itching, at the torso and on the upper and lower limbs. In order to try to overcome this problem he was prescribed a hyposodic diet that, in addition to causing arterial hypotension with syncopae episodes, did not afford any beneficial results as far as itch was concerned. Then, the patient was given antihistamines of various types, again with no appreciable results. Lastly, he underwent an additional 3 hours dialysis treatment each week, with carbon filter, for four weeks on end. Also this attempt was unsuccessful.

When starting the treatment with nicotinamide, itching persisted night and day, preventing the patient from sleeping. When clinically examined, the patient did not show any cutaneous alterations that could explain such itching, but several lesions due to scratching were present, diffused on the whole body, consisting in linear excoriations. Some of such lesions appeared to be older, with scabs due to previous bleeding. The treatment was started with 50 mg of nicotinamide twice daily, to be taken orally after the main meals. After one month and a half, pruritus had sensibly decreased. The patient continued to take 50 mg of nicotinamide after dinner for 15 more days, and then he took 50 mg of the same agent only on the day of the dialytic treatment. At the subsequent check-up, after one month, the patient still complained of some moderate itching.

Thereafter the patient was treated with the combination of 50 mg of nicotinamide+2.5 mg of riboflavin, twice daily. Itching disappeared in 5 days, and did not revert any more.

2nd case—70-years-old male subject on renal dialysis for renal failure—The patient had been on renal dialysis for about 18 months, to treat a terminal chronic renal failure. He had been complaining of a diffused pruritus extending on the whole body, which he felt during the day, but even more intensely during the night. Upon consulting the specialists of the hospital where he was undergoing dialysis, the patient did not receive any treatment that could alleviate his pruritus.

Upon undergoing an oral treatment with 50 mg of nicotinamide twice daily for 45 days on end, the patient achieved an appreciable reduction of the symptom. Thereafter, he was treated with half dose of the same agent for 15 more days, and then the treatment was finally discontinued. After 15 days, itching had started again to gradually increase.

Then the patient underwent the therapy according to the invention, with an oral administration of 50 mg of nicotinamide+2.5 mg of riboflavin twice daily. After 6 days, itching had totally disappeared. The treatment was continued for 15 more days with half the dose, and then it was discontinued. At the subsequent check, after 2 months, the patient did not report any itching.

3rd case—45-years-old female subject with persistent anal vulvar pruritus—The concerned symptoms had persisted for about 2 years. Having consulted first a gastroenterologist, the patient underwent a rectoscopy with biopsies, which did not show the presence of any pathology that could explain the itching. A rectal cortisone foam, prescribed as a possible remedy, did not result in any relief. As to the vulvar pruritus, the patient had consulted a gynaecologist who did not detect any particular pathology. She was then prescribed a therapy with vaginal douches with mild disinfectants and cortisone creams, which did not reduce itching at all. The patient was then treated with antihistamines, with no appreciable benefit. As she suffered from an allergy to antibiotics, she had also undergone all of the necessary allergy tests, but no particular allergies were evidenced. Later, a persistent itching had also appeared on the patient's face, albeit with no cutaneous lesions.

Then, the patient was given a therapy with 50 mg of nicotinamide twice daily, by oral administration, after the main meals. After 60 days itching was moderate. The patient continued to take 50 mg of nicotinamide daily, after dinner, for 15 days, and then she discontinued the treatment. After 15 days itching started to increase again, quite slightly at first, and then more remarkably.

The patient then started the oral therapy with 50 mg of nicotinamide+2.5 mg of riboflavin twice daily, and itching totally disappeared after 15 days. The treatment was then continued for 15 more days, with half the dosage, and then finally discontinued. At the subsequent check-up, after 2 months, the patient did not complain of any itching.

$4^{th}$ case—65-years-old female subject with senile pruritus—The patient had been suffering for about 2 years and a half from a diffused continuous itching at the torso and on the upper and lower limbs. Such itching became sometimes milder for one week without disappearing completely. Clinical analysis and X-ray examinations did not show the presence of any particular disease. Upon consulting some physicians, the patient underwent treatments with antimycotic, antihistamines and corticosteroids, albeit with no appreciable improvement. When the clinical test was started, the examination revealed the absence of any cutaneous alterations that could explain the itching, and the diagnosis of senile pruritus was made. Diffused lesions due to scratching were present.

The patient was then orally treated with 50 mg of nicotinamide twice daily, after the main meals, and after 40 days pruritus was quite mild. The treatment was continued with half the dose for further 15 days and then it was finally discontinued. After about 10 days, itching had started again to increase.

Then, the patient was treated with 50 mg of nicotinamide+ 2.5 mg of riboflavin twice daily, by oral administration, and after 4 days itching had disappeared. The treatment with half the dose was continued for 15 days, and then it was discontinued. At the check-up, after 2 months, the patient reported to suffer no more from hitching.

$5^{th}$ case—63-years-old male subject with chronic renal insufficiency—The patient had been suffering for about 5 years from chronic renal insufficiency, his serum creatinine level having been 3 mg/dl for about one year and a half. Thus, the patient was on a hypoproteic diet. Since about 2 years before, the patient had been affected with diffused itching of medium seriousness. He was prescribed antihistamines by the nephrologists who were treating him, and he continued such therapy for some time with no relief at all.

The patient was then treated with 50 mg of nicotinamide twice daily, orally administered after the main meals, and after 35 days he complained of some moderate itching. He had then discontinued the treatment. After about 10 days, itching had started to increase again.

Then, the treatment was changed to 50 mg of nicotinamide+2.5 mg of riboflavin twice daily, by oral administration, and after 5 days itching had totally disappeared. At the subsequent check-up, after 2 months, the patient did not complain of any itching.

$3^{rd}$ Series of Tests—Treatment with Nicotinamide Alone $1^{st}$ case—68-years-old male subject on renal dialysis three times weekly—The patient had been on dialysis three times a week for about 15 months, each treatment lasting 4 hours. He had been diagnosed chronic terminal renal insufficiency. He had been suffering from itching for about 3 years, at first at his upper limbs and then, gradually, on the whole body. The intensity of itching was steeply increasing, and no exterior signs could explain such affection. The nephrologists who were treating him had prescribed, at first, warm baths in order to moisten the skin, and then, as the symptoms were increasing, antihistamines. However, the patient could draw no benefit from such therapy.

Thereafter the patient was treated with 50 mg of nicotinamide twice daily, by the oral route, and after 65 days itching had only become milder without disappearing. The patient continued to take 50 mg of nicotinamide after each dialysis treatment. At each subsequent check-up, every 2 months, the patient complained of a persistent pruritus of a reduced intensity.

$2^{nd}$ case—61-years-old male subject with renal insufficiency—The patient had been suffering for about 3 years of renal insufficiency that was becoming increasingly serious, and was being treated by a nephrologist. The nitrogen level of his blood was 100 mg/dl, while the level of his serum creatinine was 2.8 mg/dl. About 10 months before he started to complain of a diffuse pruritus of serious intensity, which did not regress with the conventional therapies adopted by the specialists.

Then, the patient was orally treated with 50 mg of nicotinamide twice daily. After 50 days, itching had become milder, without totally disappearing. In spite of the fact that the therapy with 50 mg/day of nicotinamide was continued, at the subsequent periodical checks the patient reported a moderate itching diffused on the whole body.

$3^{rd}$ case—65-years-old female subject with senile pruritus—The patient had been suffering for about one year from a diffused itching. At first she had consulted a dermatologist, who excluded the presence of any cutaneous pathology. Then, the patient was examined by a specialist in internal medicine, who, after careful examination, could not evidence any kind of illness. As itching had increased in intensity, the patient had reverted to the dermatologist, who prescribed at first antihistamines, and then a thermal therapy. Thereafter, the diagnosis of senile itching was made.

The patient was then treated with 50 mg of nicotinamide twice daily by oral administration, and after 45 days itching had only slightly decreased. The patient continued with the prescribed therapy, and, at the subsequent monthly checks, reported about the presence of a diffused moderate itching.

$4^{th}$ case—48-years-old female subject with anal and vulvar pruritus—The patient had been complaining of the concerned symptoms for about of 18 months, the intensity of the symptoms being gradually increasing. Upon consuiting a gynaecologist, no vaginal pathology was detected. However, she had been prescribed a topical therapy with cortisone and antimycotics, albeit with no benefit. A gastroenterologist, consulted for the anal pruritus, after performing a rectoscopy, did not find any pathology that could explain the itching symptoms. She was given a topical therapy based on a cortisone foam, from which she could not draw any relief.

Then the oral treatment with 50 mg of nicotinamide twice daily was carried out, and after 2 months a decrease of the symptoms was detected. At the subsequent monthly checks, the patient still complained of a moderate itching, in spite of the fact that she was still taking 50 mg/day of nicotinamide.

The foregoing experimental report clearly shows the superior effectiveness of the vitamin combination according to the invention in the therapy of several forms of pruritus and non-infective inflammatory diseases, in comparison with similar treatments suggested by the prior art, based on nicotinamide or niacin only.

The present invention has been disclosed with particular reference to some specific embodiments thereof, but it should be understood that modifications and changes may be made by the persons skilled in the art without departing from the scope of the invention as defined in the appended claims.

The invention claimed is:

1. A method for the treatment of urticaria, asthma, allergic rhinitis, and allergic oculorhinitis, which method comprises systemically administering to the said subject an effective amount of a combination of nicotinic acid or nicotinamide and riboflavin, optionally in a pharmaceutically acceptable vehicle or carrier suitable for systemic administration, wherein said combination consists of nicotinic acid or nicotinamide and riboflavin in a ratio by weight of from 40:1 to 10:1 (nicotinic acid or niacinamide: riboflavin).

2. The method according to claim 1, wherein said combination consists of nicotinamide and riboflavin in a ratio by weight of 20:1.

3. The method according to claim 1, wherein said systemic administration is by the oral route or by the parenteral route.

* * * * *